United States Patent [19]
Khouri

[11] Patent Number: 5,395,236
[45] Date of Patent: Mar. 7, 1995

[54] ORTHODONTIC PLIERS

[76] Inventor: Suhail A. Khouri, 1879 Seven Pines Dr., St. Louis, Mo. 63146

[21] Appl. No.: 132,097

[22] Filed: Oct. 5, 1993

[51] Int. Cl.$^6$ .......................... A61C 3/00; A61C 3/14; B21F 1/00; B25B 7/02
[52] U.S. Cl. ........................ 433/4; 433/159; 140/106; 81/424.5
[58] Field of Search ............ 433/4, 159, 160; 140/102.5, 104, 106; 81/424.5, 426, 426.5

[56] References Cited
U.S. PATENT DOCUMENTS

| | | | |
|---|---|---|---|
| 715,674 | 12/1902 | Lemon | 81/426 |
| 2,954,606 | 10/1960 | Peak | 433/4 |
| 3,041,729 | 7/1962 | Tofflemire | 433/159 |
| 3,804,132 | 4/1974 | Mann | 433/4 X |
| 4,073,179 | 2/1978 | Hickey et al. | 81/426 X |
| 4,081,909 | 4/1978 | Garcia | 433/4 |

*Primary Examiner*—Nicholas D. Lucchesi
*Attorney, Agent, or Firm*—Chilton, Alix & Van Kirk

[57] ABSTRACT

The pliers in overall structure resemble conventional orthodontic pliers, but have specialized jaw members adapted to effectuate necessary gingivally directed bends in the distal ends of the arch wire. With reference to an imaginary plane along which the jaw members open and close, a first jaw member projects transversely from this plane and has a free end provided with an angulated, profile facing the longitudinal axis of the pliers. A second jaw member projects transversely to the plane, and has a free end provided with a concave, preferably angulated profile adapted to mate intimately with the convex profile when the jaws are in the closed position. Each of the profiles includes an inner surface closer to the pivot joint of the pliers, oriented perpendicularly to the plane and parallel to the pliers longitudinal axis, and an outer surface farther from the pivot, oriented perpendicularly to the plane and angled obliquely to the longitudinal axis. Preferably, the dimension of the inner surface parallel to the longitudinal axis, is less than the dimension of the outer surface along the oblique angle. Preferably, the outer surface is about 2.5 mm in length, and the inner surface about 0.5 mm in length, defining a ratio of approximately 5 to 1.

11 Claims, 3 Drawing Sheets

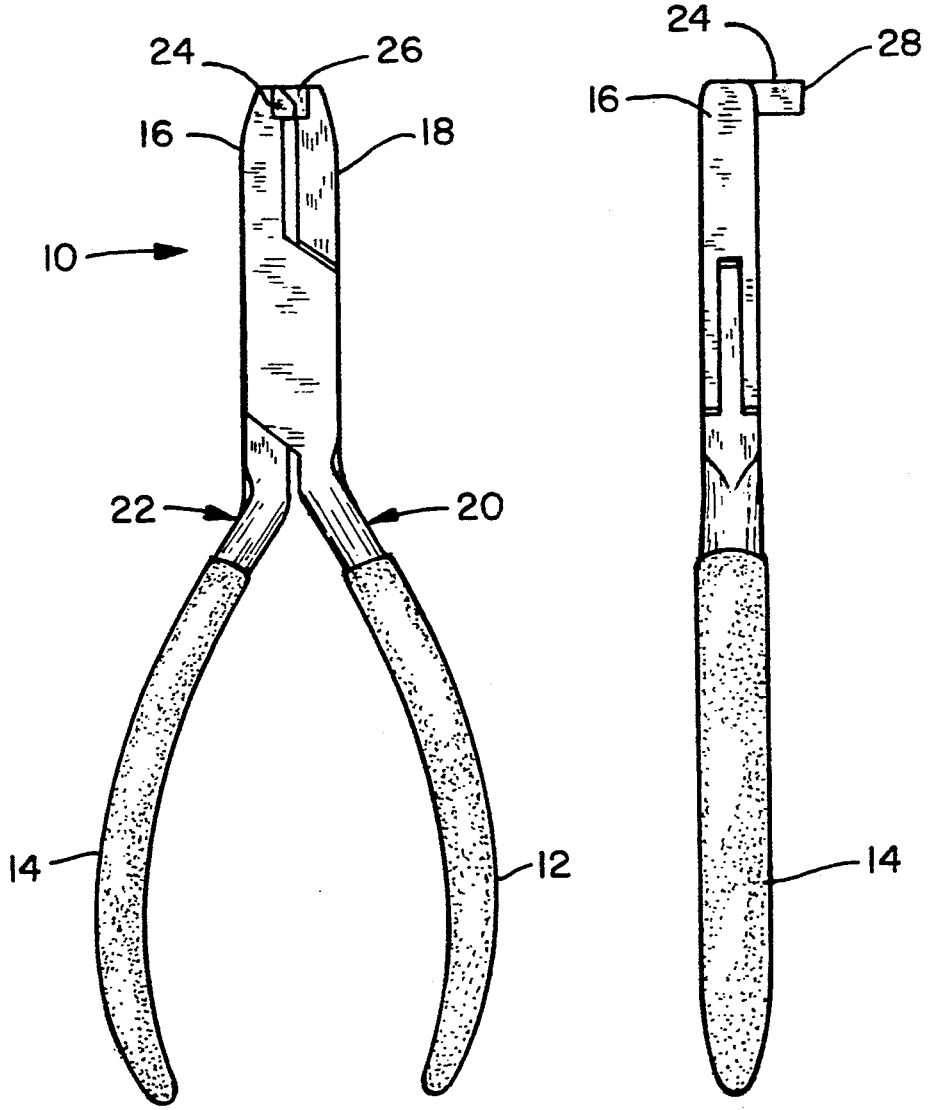

ORTHODONTIC PLIERS

BACKGROUND OF THE INVENTION

The present invention relates to orthodontic pliers, and more particularly, to apparatus and method for bending the distal end of orthodontic arch wires.

Stabilization of orthodontic arch wires against anteroposterior slippage and the protection of oral tissues from puncture type injuries are an important consideration in the installation of any orthodontic appliance. Conventionally, such objectives are accomplished by adding either welded stops, omega loops or helices to the design of the arch wires so that they may be tied back to molar brackets. It is well known that adding such an essential modification to arch wires requires technical precision and consumes extra clinical and laboratory time. Since the reduction of chain side time has become a driving force for many recent innovations in orthodontic techniques and the appliance industry, most orthodontists began to use distal-end bending as a faster, easier and effective alternative to the conventional tie back techniques. Howe pliers, or tie-back pliers, have been used successfully to bend distal ends of the preformed arch wires as they project from bracket tubes of cemented molar bands.

With the use of bondable molar brackets and, more recently, highly flexible wires, the conventional pliers of the type described above for bending distal ends of flexible arch wires projecting out of bondable molar brackets has been found to be ineffective. The use of conventional pliers often leads to debonding of those brackets and subsequently to failure of the bending procedure. The time required to rebond molar brackets negates any time saving from bending distal ends.

Some reasons for the debonding of molar brackets with the use of currently available pliers include the insufficient angularion of the pliers' jaws to allow comfortable and effective grip of the posteriorly projected distal ends. This is due to the limited accessibility of distal ends far back in the buccal vestibule area. Additionally, poor visibility in that area may result in clumsy or accidental squeezing of the bracket that often leads to the bracket debonding. In addition, the necessary overbending of distal ends of the highly flexible wires renders this bending procedure difficult for the operator and annoying to the patient. Over-bending of the short distal ends of the arch wires against the distal edge of the bonded bracket tube acting as a fulcrum, creates a dislodging shearing torque, acting on the bracket and leading to its debonding.

As a result of the inavailability of precise pliers, a prolonged, rather than shortened time is often needed to untie and remove the arch wire and rebond the displaced bracket. In order to reliably and efficiently utilize the orthodontic procedure of distal end bending employing highly flexible wires and bondable molar brackets, these problems must be overcome.

SUMMARY OF THE INVENTION

In accordance with the present invention, a new pliers design is provided which successfully bend with one or two firm squeezes, the distal ends of all types and sizes of arch wires, including the highly flexible ones. The pliers can be utilized far back in the limited buccal vestibule, without interfering with molar bracket bonding. The pliers perform this function with minimal clinical time and ultimate convenience to the operator and the patient.

The pliers in overall structure resemble conventional orthodontic pliers, but have specialized jaw members adapted to effectuate necessary gingivally directed bends in the distal ends of the arch wire. With reference to an imaginary plane along which the jaw members open and close, a first jaw member projects transversely from this plane and has a free end provided with an angulated profile facing the longitudinal axis of the pliers. A second jaw member projects transversely to the plane, and has a free end provided with an angulated profile adapted to mate intimately with the other profile when the jaws are in the closed position. Each of the profiles includes an inner surface closer to the pivot joint of the pliers, oriented perpendicularly to the plane and parallel to the pliers longitudinal axis, and an outer surface farther from the pivot, oriented perpendicularly to the plane and angled obliquely to the longitudinal axis. Preferably, the dimension of the inner surface parallel to the longitudinal axis, is less than the dimension of the outer surface along the oblique angle. Preferably, the outer surface is about 2.5 mm in length, and the inner surface about 0.5 mm in length, defining a ratio of approximately 5 to 1.

The pliers according to the invention are provided in a set of two, to facilitate a gingivally directed bend of the arch wires in each of the four quarters of the patient's mouth. By using the set of two pliers, access to the respective ends of the arch wires can always be made from the front of the mouth of the patient, with the patient's mouth only half-open.

BRIEF DESCRIPTION OF THE DRAWINGS

The preferred embodiment of the invention will be described below with reference to the accompanying drawings, in which:

FIG. 1 is a plan view of one pair of pliers in accordance with the invention;

FIG. 2 is a side view of the pliers shown in FIG. 1, taken along a direction from the left side of FIG. 1;

DESCRIPTION OF THE PREFERRED EMBODIMENT

Figure 3:
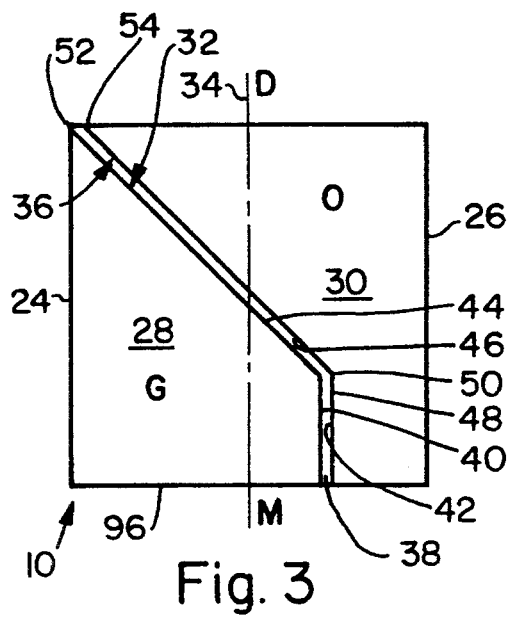
FIG. 3 is a section view of the upper portion of the jaws of the pliers.

FIGS. 1 and 2 show one pair of orthodontic pliers 10 in accordance with the invention, having first 12 and second 14 handle portions connected pivotally, with corresponding first 16 and second 18 nose portions that can be opened and closed along, or parallel to, an imaginary plane. The first handle 12 and first nose 16, and second handle 14 and second nose 18, are in effect, first and second actuating members 20,22 for moving first and second jaws 24,26 between opened and closed positions.

When the jaws 24,26 are in the closed position, the first 16 and second 18 nose portions are substantially parallel to the longitudinal axis of the pliers, which passes through the pivot. The first and second jaw members 24,26 extend transversely, preferably perpendicularly, to the longitudinal axis and the imaginary plane. Each jaw member 24,26 has a free end 28,30 which extends approximately 8 mm from the respective nose portions.

Figure 5:
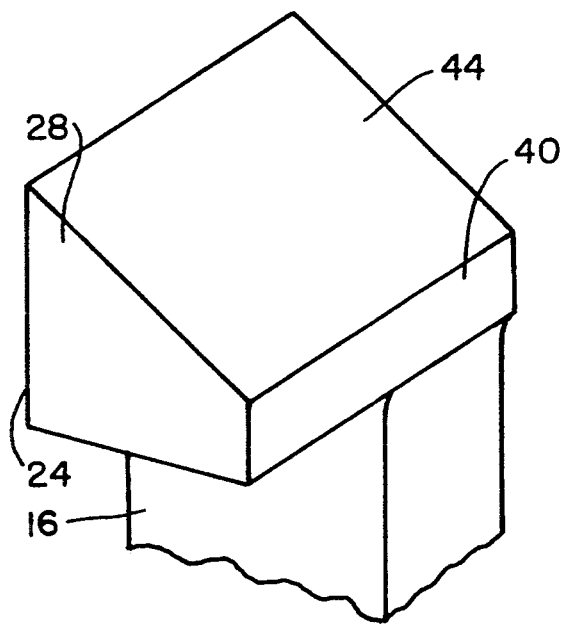
FIG. 5 is a perspective view of one jaw shown in FIG. 3.

As shown in FIGS. 3 and 5, the first, or gingival jaw 24, has an externally angled profile 32 generally facing the longitudinal axis 34, and the second, or occlusal jaw member 26 has an internally angled profile 36 generally facing the longitudinal axis and adapted to mate with the profile 32 of the first jaw member when the nose portions are in the closed position. Preferably, the jaws 24,26 do not actually touch each other in the closed position, but rather maintain a substantially uniform spacing 38 which is approximately equal to or less than the diameter of a typical arch wire. Each jaw member 24,26 has a respective inner (medial) surface 40,42 closer to the pivot and an outer (distal) surface 44,46 farther from the pivot, both surfaces being oriented substantially perpendicularly to the imaginary plane on which the noses 16,18 of the pliers open and close. Preferably, these surfaces are uniform, i.e., flat, over the full height of the jaw members from the connection to the nose 16 to the free ends thereof 30.

The inner surfaces 40,42 of the gingival and occlusal jaw members respectively, are preferably oriented parallel to the pliers axis 34, when the jaws are closed, and located laterally of the axis 34. At the distal extremities 48,50 of the inner surfaces 40,42, the outer surfaces 44,46 extend obliquely (i.e., at a uniform angle) to the longitudinal axis 34. Preferably, the cross section of the jaws 24,26 together in the closed position is substantially rectangular or square, and the distal extremities 52,54 of the outer surfaces 44,46 terminate substantially at a corner of the square or rectangle formed by jaws 24,26 together.

In use, the inner surfaces 40,42 grasp the arch wire substantially along the arch wire axis (not shown) whereas the outer surface 46 of the occlusal jaw 26 will bend the distal end of the arch wire toward, and eventually in contact with, the outer surface 44 of the gingival jaw member 24, thereby producing the required gingival bend. Preferably, the dimension of the flat inner surfaces 40,42 parallel to the pliers axis 34 is less than the dimension of the flat outer surfaces 44,46 in the oblique direction, with the preferred lengths of 0.5 mm and 2.5 mm, respectively, i.e., a ratio of about one to five.

Figure 4:
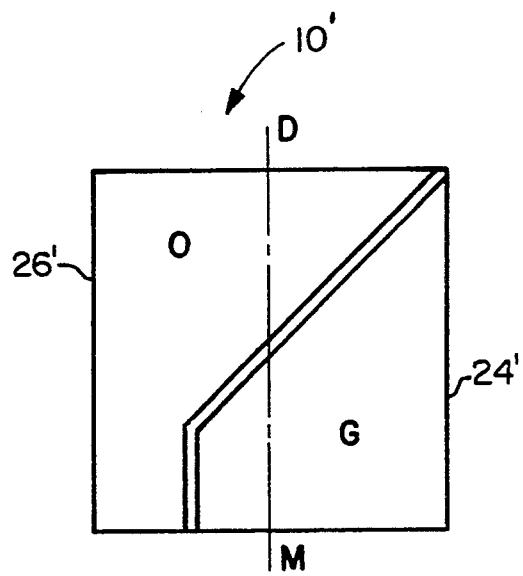
FIG. 4 is an equivalent section view to that shown in FIG. 3, through the jaws of the other pliers in the set.

It should be appreciated that in the preferred embodiment of the invention, two pliers 10,10' are provided, the jaws 24',26' of the second pliers 10' being shown schematically in FIG. 4, as a mirror image of the jaws shown in FIG. 3. This allows use in the alternate quadrants of the mouth.

Figure 6:
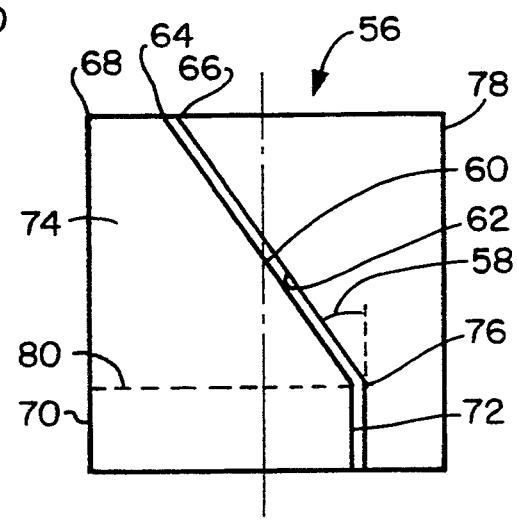
FIG. 6 is an alternative embodiment of the jaws shown in FIG. 3.

Variations of the preferred embodiment may also be utilized, for example as shown in FIG. 6. In the embodiment 56 of FIG. 6, the oblique angle 58 of the outer surfaces 60,62 is only about 30 degrees versus 45 degrees in the embodiment shown in FIG. 3. As a result, the distal end extremities 64,66 of the outer surfaces do not pass through the "corner" 68 of the square jaw envelope created by jaws 68,70 together as viewed in section.

It should be appreciated that a workable, although not preferred embodiment can also be achieved by eliminating all or most of the portion 74 of the gingival jaw 70 located distally of the inner surface thereof 72. The important consideration is the provision of a solid inner surface 72 on the gingival jaw 70, about which the inner corner 76 on the occlusal jaw 78 can bend the arch wire. The outer surface 62 of the occlusal jaw is required to effectuate this bending, whereas the outer surface 60 on the gingival jaw is not absolutely necessary. Thus, the portion 74 of the gingival jaw in FIG. 6 located distally of the dashed line 80, could be eliminated in another embodiment of the invention.

The method in accordance with the invention can best be understood with further reference to FIGS. 7–11. Any excess wire projecting distally to the molar tube 82 is cut on both sides, after the arch wire 84 has been seated in place. Two or three mm of projecting wire length 86 is left, to assure a reasonable grip with the pliers 10. The patient is asked to open the mouth slightly to facilitate accommodation of the pliers in the buccal vestibule. This is important because opening wide brings the anterior border of the mandibular ramus forward and blocks the buccal vestibular accessibility to the molar tubes. Some patients must close their teeth in order to gain better buccal vestibular accessibility.

The appropriate one of the pair of pliers 10, or 10' is selected to secure a gingivally directed bend for the involved quarter. The jaw members are preferably marked as occlusal and gingival, whereby the occlusal jaw is always placed occlusally and the gingival jaw always gingivally. Therefore, the pliers 10' used for the maxillary left molar 88 serve also for the mandibular right molar, and the pliers 10 used for the maxillary right molar 92 serve for the mandibular left molar 94, as shown in FIGS. 8–11.

Figure 7:
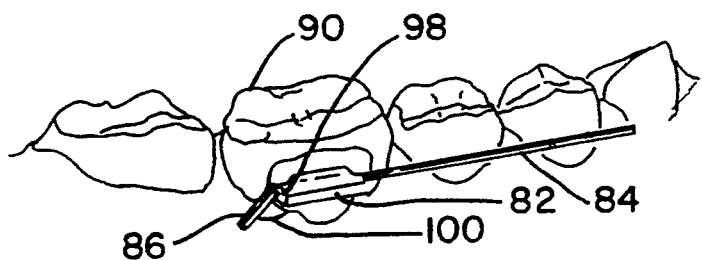
FIG. 7 is an artistic rendition of a dental arch wire assembly secured to the teeth of the lower right quadrant.
Figure 8:
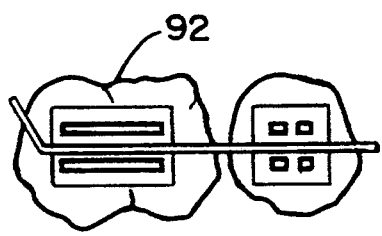
FIG. 8 is a schematic view of the molar bracket, arch wire and distal bend associated with the upper right quadrant.
Figure 9:
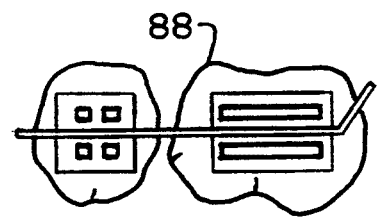
FIG. 9 is a view similar to FIG. 8 for the upper left quadrant.
Figure 10:
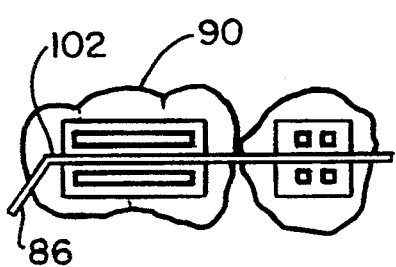
FIG. 10 is a view similar to FIG. 8 for the lower right quadrant.
Figure 11:
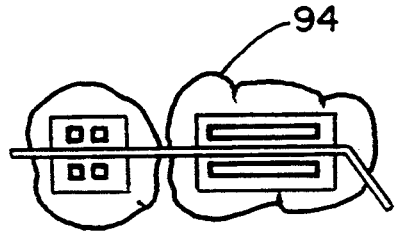
FIG. 11 is a view similar to FIG. 8 for the lower left quadrant.

As evident from FIGS. 3 and 7, the selected pliers are placed in the buccal vestibule with the projecting jaws 24,26 toward the teeth, and the handles 12,24 vertically in the palm of the operator. The mesial aspect 96 of the slightly open jaws 24, 26 are placed gently to gain intimate contact with the distal aspect 98 of the tube 82, with the distal projection 86 of the arch wire 84 loosely gripped between the jaws 24,26. The axis 34 of the pliers 10 should be in line with the anteroposterior direction of the wire projection 86. This is important to assure that the fulcrum point of the bending force will remain located on the distal aspect 98 of the tube.

Once these positions have been secured, the pliers 10 is firmly squeezed in the hand to obtain an adequate bend. Two or three squeezes may be needed to obtain the desired bend angulation 100. With the preferred embodiment, the resulting bend is gingivally directed and located 0.5 mm 102 from the bracket or tube 82. The bend 100 will serve as an effective means of arch wire back-holding which will lie safely in line with the buccal sulcus behind the molar tube. Sometimes, due to unfavorable tilt in the vertical position of the pliers 10 during the squeezing procedure, the bend 100 may be directed buccally, causing buccal mucosal irritation. To deal with this possibility, the counterpart pliers 10' are placed in the buccal vestibule with the projecting jaws 24',26' toward the teeth and a slight lateral orientation of the jaw and a squeeze to bend the projecting end 86 of the wire 84 gingivally, but towards the teeth rather than towards the cheeks.

I claim:

1. A pair of orthodontic pliers for installing dental arch wires, comprising:

first and second elongated actuating members, each actuating member including a handle portion for grasping in the hand, and a nose portion for positioning adjacent the dental arch wires, the actuating members being pivotally joined intermediate the handle portions and the nose portions so that the nose portions can be moved toward and away from each other into respective closed and open positions substantially along an imaginary plane by manipulating the handles about a longitudinal axis;

a first jaw member projecting transversely to said plane and from only one side thereof, from the nose portion of the first actuating member, and having an externally angled profile facing the longitudinal axis;

a second jaw member projecting transversely to said plane and from only said side thereof, from the nose portion of the second actuating member, and having an internally angled profile adapted to mate with said externally angled profile when the nose portions are in the closed position;

each of said profiles including an inner surface located closer to the pivot and oriented perpendicularly to the imaginary plane and parallel to the longitudinal axis, and an outer surface farther from the pivot and oriented perpendicularly to the imaginary plane and angled obliquely to the longitudinal axis.

2. The orthodontic pliers of claim 1, wherein the dimension of each inner surface parallel to the longitudinal axis is less than the dimension of each outer surface along said oblique angle.

3. The orthodontic pliers of claim 2, wherein said dimension of each outer surface is about five times greater than said dimension of each inner surface.

4. The orthodontic pliers of claim 1, wherein the jaw members are arranged such that when the nose portions are in the closed position, the profiles are juxtaposed with a gap therebetween that is no greater than the approximate diameter of each arch wire.

5. The orthodontic pliers of claim 1, wherein the jaw members project from the respective nose portions perpendicularly to the imaginary plane.

6. The orthodontic pliers of claim 5, wherein the profiles consist of angled flat surfaces provided over substantially the entire projecting lengths of the respective jaw members.

7. The orthodontic pliers of claim 6, wherein the jaw members when viewed together in a direction perpendicular to the imaginary plane, define a substantially rectangular perimeter when the nose portions are in the closed position.

8. The orthodontic pliers of claim 1, wherein said inner surfaces of the profiles are flat and extend parallel to the longitudinal axis, for a distance of about 0.5 mm.

9. A method of completing the installation of an orthodontic arch wire, secured to a bracket member on a molar by using a pair of pliers having gingival and occlusal jaw members, comprising the steps of:

trimming the arch wire to a projection length of at least 2.0 mm distally of the bracket;

positioning the gingival jaw member against the distal aspect of the bracket and on the gingival side of the projecting arch wire;

positioning the occlusal jaw member against the distal aspect of the bracket and on the occlusal side of the projecting arch wire, said gingival and occlusal jaw members having respective first flat surfaces adjacent the bracket, which are parallel to the distally projecting arch wire when the jaws are in the closed position and said occlusal jaw member having a second surface extending from the first surface and angled obliquely toward the gingival jaw member;

closing the jaw members by advancing the occlusal jaw member relatively toward the gingival jaw member, whereby a portion of the distally projecting arch wire adjacent the bracket is stabilized between said first surfaces and the remainder of said projecting arch wire is bent gingivally at said oblique angle.

10. The method of claim 9, wherein the step of closing the jaw member includes stabilizing a portion of the projecting arch wire over a length of about 0.5 mm from the bracket.

11. The method of claim 9, wherein the step of closing the jaw members includes said second angled, surface on the occlusal jaw member moving toward a second angled surface extending obliquely from the first surface of the gingival jaw member.

* * * * *